(12) United States Patent
Polonka et al.

(10) Patent No.: US 7,776,350 B2
(45) Date of Patent: Aug. 17, 2010

(54) SUNSCREEN COMPOSITE PARTICLES IN COSMETIC COMPOSITIONS

(75) Inventors: Jack Polonka, Peekskill, NY (US); John Brian Bartolone, Bridgeport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 95 days.

(21) Appl. No.: 12/164,135

(22) Filed: Jun. 30, 2008

(65) Prior Publication Data

US 2009/0324652 A1 Dec. 31, 2009

(51) Int. Cl.
*A61K 8/02* (2006.01)
*A61K 8/00* (2006.01)

(52) U.S. Cl. .......................... 424/401; 424/59

(58) Field of Classification Search ................ 424/401
See application file for complete search history.

(56) References Cited

U.S. PATENT DOCUMENTS

| | | | |
|---|---|---|---|
| 3,895,104 A | 7/1975 | Karg | |
| 4,731,242 A | 3/1988 | Palinczar | |
| 5,264,207 A | 11/1993 | Bommelaer et al. | |
| 5,733,531 A | 3/1998 | Mitchnick et al. | |
| 5,783,657 A | 7/1998 | Pavlin et al. | |
| 5,972,359 A | 10/1999 | Sine et al. | |
| 5,997,890 A | 12/1999 | Sine et al. | |
| 5,998,570 A | 12/1999 | Pavlin et al. | |
| 6,036,945 A | 3/2000 | Deblasi et al. | |
| 6,174,533 B1 | 1/2001 | SaNogueira, Jr. et al. | |
| 6,242,509 B1 | 6/2001 | Berger et al. | |
| 6,280,710 B1 | 8/2001 | Deblasi et al. | |
| 6,399,713 B1 | 6/2002 | MacQueen et al. | |
| 6,402,408 B1 | 6/2002 | Ferrari | |
| 6,492,458 B1 | 12/2002 | Pavlin | |
| 6,552,160 B2 | 4/2003 | Pavlin | |
| 6,592,857 B2* | 7/2003 | Lawson et al. | 424/70.122 |
| 6,685,966 B1 | 2/2004 | Dominique et al. | |
| 6,835,399 B2 | 12/2004 | Collin | |
| 6,870,011 B2 | 3/2005 | MacQueen et al. | |
| 6,875,245 B2 | 4/2005 | Pavlin | |
| 7,067,152 B2* | 6/2006 | Shefer et al. | 424/490 |
| 7,253,249 B2 | 8/2007 | Pavlin | |
| 7,264,795 B2* | 9/2007 | Pflucker et al. | 424/59 |
| 7,329,719 B2 | 2/2008 | Pavlin | |
| 7,351,418 B2 | 4/2008 | Collin | |
| 2005/0031658 A1 | 2/2005 | Girier Dufournier et al. | |
| 2005/0163730 A1* | 7/2005 | Rosevear et al. | 424/59 |
| 2005/0163813 A1 | 7/2005 | Kosbach et al. | |
| 2005/0191491 A1* | 9/2005 | Wang et al. | 428/407 |
| 2005/0197479 A1 | 9/2005 | Pavlin | |
| 2005/0249684 A1 | 11/2005 | Dobkowski et al. | |
| 2005/0276833 A1 | 12/2005 | Fowler | |
| 2006/0099168 A1 | 5/2006 | Corzani et al. | |
| 2006/0280763 A1 | 12/2006 | Yoshida et al. | |
| 2007/0212315 A1 | 9/2007 | Pastor et al. | |
| 2008/0095852 A1* | 4/2008 | Kong et al. | 424/489 |
| 2008/0115846 A1 | 5/2008 | Josso et al. | |
| 2009/0016971 A1 | 1/2009 | Gaudry et al. | |

FOREIGN PATENT DOCUMENTS

| | | |
|---|---|---|
| EP | 0 904 768 A1 | 9/1998 |
| EP | 1 388 550 A1 | 8/2003 |
| EP | 1 475 078 A1 | 5/2004 |
| EP | 1 642 924 A1 | 9/2005 |
| EP | 1 813 266 A1 | 12/2006 |
| EP | 2 005 940 A2 | 6/2008 |
| GB | 2 166 107 A | 4/1986 |
| WO | 01/87847 A2 | 11/2001 |

OTHER PUBLICATIONS

Dagani, R. Science/Technology (Putting the 'Nano∝ Into Composites), vol. 77, No. 23, Cenear 77 23 pp. 25-37, printed pp. 1-19).*
Co-Pending Application—Polonka et al.; U.S. Appl. No. 12/330,740, filed Dec. 9, 2008; entitled: Sunscreen Composite Particles.
Co-Pending Application: Polonka et al.; Entitled: Sunscreen Composite Particles Dispersed in Water-In-Oil Cosmetic Compositions.
Co-Pending Application: Polonka et al.; Entitled: Sunscreen Composite Particles and Porous Particles in Cosmetic Compositions.
Co-Pending Application: Polonka et al.; Entitled: Sunscreen Formula Vanishing Cream.
PCT International Search Report PCT/EP2009/057154.
PCT Written Opinion PCT/EP2009/057154.

* cited by examiner

*Primary Examiner*—Sreeni Padmanabhan
*Assistant Examiner*—Timothy E Betton
(74) *Attorney, Agent, or Firm*—Milton L. Honig

(57) ABSTRACT

A cosmetic composition is provided which includes hydrophilic composite particles of an organic sunscreen agent, particles of a crosslinked silicone elastomer, and a cosmetically acceptable carrier. The hydrophilic composite particles are formed as a composite of sunscreen agent and binder in a relative weight ratio of about 5:1 to about 1:10. The composition exhibits relatively high SPF photoprotection while maintaining excellent soft focus properties that hide skin imperfections.

7 Claims, No Drawings

SUNSCREEN COMPOSITE PARTICLES IN COSMETIC COMPOSITIONS

BACKGROUND OF THE INVENTION

1. Field of the Invention

The invention concerns cosmetic sunscreen compositions delivering UV protection and also soft focus properties.

2. The Related Art

Ultraviolet radiation can be damaging to skin. Immediate damage may be in the form of erythema. More long term is the concern of initiating cancerous growth. For these reasons, photoprotective agents known as sunscreens have been incorporated into cosmetic products.

Facial cosmetics desirably deliver not only photoprotection but also function to enhance overall skin appearance. Most persons have facial imperfections. These may include uneven tone, enlarged pores, fine lines and wrinkles.

Soft focus is a technique which can hide imperfect skin. Incoming light is distorted by scattering (lensing). Particulate components of the cosmetic operate as lenses to bend and twist light into a variety of directions.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

U.S. Patent Application 2005/0163813 A1 (Kosbach et al.) reports use of fumed alumina particles for enhancing the soft-focus effect of certain cosmetic compositions.

Crosslinked silicone elastomers also have been identified as aids in achieving soft focus. U.S. Patent Application 2005/0163730 A1 (Rosevear et al.) discloses a synergistic interaction between crosslinked silicone elastomer and zinc oxide having average particle size less than 300 nm. A related disclosure is found in U.S. Patent Application 2005/0249684 A1 (Dobkowski et al.) wherein a taurate polymer enhances optical effects in combination with a silicone elastomer and zinc oxide.

A disadvantage of silicone elastomers is their interaction with organic sunscreens. Generally the silicone elastomers are suspended/dissolved in a silicone fluid carrier. These silicone fluid carriers are extractable into the organic sunscreens thereby shriveling the elastomer particles adversely affecting soft focus properties. Consequently, there is a challenge to provide a soft focus effect while maintaining a relatively high degree of photo protective properties in a cosmetic composition.

SUMMARY OF THE INVENTION

A cosmetic composition is provided which includes:
(i) from about 0.1 to about 20% by weight of hydrophilic composite particles formed of an organic sunscreen agent and a binder in a relative weight ratio of about 5:1 to about 1:10;
(ii) from about 0.1 to about 30% by weight of particles of a crosslinked silicone elastomer; and
(iii) a cosmetically acceptable carrier.

DETAILED DESCRIPTION OF THE INVENTION

Now it has been found that the soft focus effect imparted through particles of a crosslinked silicone elastomer can be retained in a sunscreen composition having a high sunscreen protective factor (SPF). Photoprotection is accomplished through hydrophilic composite particles formed of a binder and an organic sunscreen agent.

Hydrophilic Composite Particles of Sunscreen Agent

Composite particles of the present invention will have a hydrophilic outer surface. Hydrophilicity may be achieved through use of a hydrophilic binder or via a hydrophilic coating such as a silica or alumina coating. The binder may be hydrophilic or hydrophobic. Suitable categories of binder are polymers such as polyacrylates, polyvinylpyrrolidones, polyesters, polyamides, polyethers, polyolefins, polysaccharides including cellulose derivatives, starches, clays, hydrocarbons and combinations thereof. Sunscreen agents can either be dispersed throughout the binder or can be formed as a core surrounded by binder.

Relative weight ratio of organic sunscreen agent to binder may range from about 5:1 to 1:10, preferably from about 3:1 to about 1:8, more preferably from about 2:1 to about 1:7, optimally from about 1:1 to about 1:3. Amounts of the binder may range from about 10% to about 99.5% by weight of the hydrophilic composite particles. More preferably weight of the binder may range from about 30% to about 98%, optimally from about 50 to about 85% by weight of the hydrophilic composite particles. Amounts of the sunscreen agent may range from about 0.5 to about 90%, preferably from about 2 to about 70%, optimally from about 30 to about 50% by weight of the hydrophilic composite particles.

Amounts of the hydrophilic composite particles within the cosmetic emulsion composition may range from about 0.1 to about 30%, preferably from about 2 to about 15%, optimally from about 4 to about 10% by weight of the cosmetic composition.

Average particle size of the hydrophilic particles may range from about 10 to about 2,000 nm, preferably from about 100 to about 1,500 nm, and optimally from about 200 to about 1000 nm.

Sunscreen agents according to this invention will have at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4, 4'-dimethoxybenzophenone, Octabenzone; 4-Isopropyldibenzoylmethane; Butylmethoxydibenzoylmethane; Etocrylene; and 4-isopropyl-dibenzoylmethane).

Particularly useful sunscreen agents are: 2-ethylhexyl p-methoxycinnamate, 4,4'-t-butyl methoxydibenzoylmethane, 2-hydroxy-4-methoxybenzophenone (known also as Benzophenone-3), octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, 4-methylbenzylidene camphor, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, terephthalidene dicamphor sulfonic acid and mixtures thereof.

Cosmetic compositions of this invention may not only have sunscreen agent held within but an amount of sunscreen agent may be formulated free of binder within the composition. When present outside the composite, the sunscreen agent may be available in amounts from about 0.1 to about 25%, particularly from about 2 to about 15% by weight of the composition. Some preferred embodiments of this invention may be formulated without any sunscreen agent external to the composites or with only a relatively small amount external to the composite particles. For instance, the external sunscreen agent may range in amount from about 0 to 5%, preferably from 0.01 to 2%, and possibly from 0.01 to 0.8% by weight of the composition.

A number of hydrophilic composite particles with sunscreen agent are commercially available. A first commercial material is known as "Sun Caps" sold by Particle Sciences, Inc. of Bethlehem, Pa. Average particle size is reported to be approximately 250 nm. Sun Caps 664 is sold with a concentration of octylmethoxycinnamate (OMC) of 21.5% encapsulated in a binder that includes beeswax, carnauba wax, Vinyl Pyrrolidone/Eicosene Copolymer and emulsifiers (PEG-100 stearate, PEG-20, bis-PEG-12 dimethicone, sorbitan tristearate and Steareth-100). Sun Caps™ are formed in a process revealed in U.S. Pat. No. 5,733,531 herein incorporated by reference. The encapsulates are supplied as an aqueous dispersion containing up to 65% solids.

Another hydrophilic composite particulate commercially available is sold by Rona Division of EMD Chemicals under the trademark Eusolex® UV-Pearls™ OMC. UV Pearls are prepared and described in U.S. Pat. No. 7,264,795 herein incorporated by reference. These composites are delivered as 40% particles delivered in 60% aqueous carrier. The particles are structured with a core of greater than 70% octylmethoxycinnamate surrounded by a coating of about 10% silica, about 1-2% polyvinylpyrrolidone (as binder), and minor ingredients.

Another useful hydrophilic composite particulate according to the present invention utilizes a binder which is a condensation polymerized polyamide resin, and especially an ester-terminated polyamide resin. A preferred embodiment of this binder is a polyalkyleneoxypolyamide (referred to as an PAOPA resin) and also an ester-terminated poly(ester-amide) (referred to as an EPTEA resin). The PAOPA resin can be prepared by reacting a monocarboxylic acid, a diamine compound, and a diacid. The EPTEA resin can be prepared by reacting a dibasic acid, a diamine, a polyol and a mono alcohol. Preferably the EPTEA resin may be formed from reaction of: (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol. Preparation and description of these resins is found in U.S. Pat. No. 7,329,719 B2 and U.S. Pat. No. 6,492,458 herein incorporated by reference. Particularly preferred are resins under the commercial trademark Sylvaclear PA 1200V, identified by INCI name of Polyamide-3, and Sylvaclear AF 1900V sold by Arizona Chemical Company, Jacksonville, Fla. These resins are easily intimately mixed with OMC to form a composite particulate with photoprotective sunscreen.

Crosslinked Silicone Elastomer

A component of the present invention is a crosslinked silicone (organopolysiloxane) elastomer. No specific restriction exists as to the type of curable organopolysiloxane that can serve as starting material for the crosslinked silicone elastomer. Examples in this respect are addition reaction-curing organopolysiloxane which cure under platinum metal catalysis by the addition reaction between SiH-containing diorganopolysiloxane and organopolysiloxane having silicon-bonded vinyl groups; condensation-curing organopolysiloxane which cure in the presence of an organotin compound by a dehydrogenation reaction between hydroxyl terminated diorganopolysiloxane and SiH-containing diorganopolysiloxane; condensation-curing organopolysiloxane which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane are preferred for their rapid curing rates and excellent uniformity of curing. A particularly preferred addition reaction-curing organopolysiloxane is prepared from:

(A) an organopolysiloxane having at least 2 lower alkenyl groups in each molecule;

(B) an organopolysiloxane having at least 2 silicon-bonded hydrogen atoms in each molecule; and (C) a platinum-type catalyst.

The crosslinked siloxane elastomer of the present invention may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxanes available under the INCI names of dimethicone/vinyl dimethicone crosspolymer, dimethicone crosspolymer and Polysilicone-11. Ordinarily these materials are provided as a 1-30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15, 16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silesquioxane crosspolymers from Shin-Etsu sold as KSP-100, KSP-101, KSP-102, KSP-103, KSP-104, KSP-105, and hybrid silicone powders that contain a fluoroalkyl group or a phenyl group sold by Shin-Etsu as respectively KSP-200 and KSP-300.

The crosslinked silicone elastomers of the present invention may range in concentration from about 0.1 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products 9040 and 9045. For instance, the amount of crosslinked silicone elastomer in 9040 and 9045 is between 12 and 13% by weight.

Most preferred as the silicone elastomer is 9045 which has a D5 cyclomethicone swelled elastomer particle size (based on volume and calculated as spherical particles) which averages about 38 micron, and may range from about 25 to about 55 micron.

Cosmetically Acceptable Carrier

Compositions of the present invention will include a cosmetically acceptable carrier. The carrier may be a liquid or solid material. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Of importance for incorporating the silicone elastomers into the compositions is the presence of a fluid silicone as a carrier. The silicone carrier, when combined with the crosslinked organopolysiloxane elastomer particles serves to suspend and swell the elastomer particles to provide an elastic, gel-like network or matrix. The carrier for the crosslinked siloxane elastomer is liquid under ambient conditions, and preferably has a low viscosity to provide for improved spreading on the skin.

Concentrations of the fluid silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and di-glycerides may also be useful. Illustrative of these categories are glyceryl monostearate and glyceryl distearate.

The carriers can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyidimethyl Taurate (e.g. Simulgel® NS and INS 100), Acrylate/Sodium Acryloyldimethyl Taurate (e.g. Simulgel® EG), Sodium Acryloyldimethyl Taurate (e.g. Simulgel® 800) and Ammonium Acryloyldimethyl Taurate/Vinyl Pyrrolidone (e.g. Aristoflex® AVC).

c. Polyacrylamide Polymers

The compositions of the present invention can optionally comprise vinyl polymerized polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

The compositions of the present invention may contain one or more particulate materials. Nonlimiting examples of particulate materials include colored and uncolored pigments, interference pigments, inorganic powders, organic powders, composite powders, optical brightener particles, and combinations thereof. Particulate materials may be present from about 0.01% to about 20%, more preferably from about 0.05% to about 10%, still more preferably from about 0.1% to about 5%, by weight of the composition.

Particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, barium sulfate, calcium carbonate, cellulose acetate, PTFE, polymethyl methacrylate, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

Other Optional Components

The composition of the present invention may contain a variety of components to enhance physical properties and performance.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, anti-foaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The compositions of the present invention may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The cosmetic compositions of the subject invention include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Examples 1-4

The following are non-limiting examples of sunscreen compositions according to the present invention.

|  | Example | | | |
|---|---|---|---|---|
|  | 1 | 2 | 3 | 4 |
| Phase A | | | | |
| DC-9040 ™ | 8.60 | 3.00 | 37.00 | 5.00 |
| Sun Caps 664 ™ | 5.00 | 6.50 | — | — |
| UV Pearls ™ | — | — | 5.00 | 6.50 |
| Benzophenone-3 | 3.00 | 3.00 | 3.00 | 3.00 |
| Polymethylsilsequioxane[2] | 4.00 | 4.00 | 4.00 | 4.00 |
| Cyclomethicone | 11.43 | 0.50 | 8.22 | 11.33 |
| Dimethicone PEG-10/15 Crosspolymer | 5.37 | 5.25 | 2.75 | 5.40 |

-continued

| | Example | | | |
|---|---|---|---|---|
| | 1 | 2 | 3 | 4 |
| Polyethylene wax | 3.54 | | 2.41 | 2.05 |
| Fragrance | 0.10 | 0.10 | 0.10 | 0.10 |
| Titanium Dioxide (Coated With 5% Dimethicone) | — | — | — | 0.65 |
| Titanium Dioxide (Coated Mica Coated with 6% Methicone) | 5.00 | 0.01 | 1.00 | — |
| Phase B | | | | |
| Glycerin | 10.00 | 10.00 | 10.00 | 10.00 |
| Dexpanthenol | 0.50 | 0.50 | 0.50 | 0.50 |
| Pentylene Glycol | 3.00 | 3.00 | 3.00 | 3.00 |
| Hexamidine Disethionate | 0.10 | 0.10 | 0.10 | 0.10 |
| Niacinamide | 5.00 | 5.00 | 5.00 | 5.00 |
| Methylparaben | 0.20 | 0.20 | 0.20 | 0.20 |
| Ethylparaben | 0.05 | 0.05 | 0.05 | 0.05 |
| Sodium citrate | 0.20 | 0.20 | 0.20 | 0.20 |
| Citric Acid | 0.03 | 0.03 | 0.03 | 0.03 |
| Sodium Benzoate | 0.05 | 0.05 | 0.05 | 0.05 |
| Sodium Chloride | 0.50 | 0.50 | 0.50 | 0.50 |
| FD&C Red #40 (1%) | 0.05 | 0.05 | 0.05 | 0.05 |
| Water | Qs | Qs | Qs | Qs |

The formulas in the examples are prepared in a suitable container first by combining the ingredients of Phase A. In a separate suitable container, combine the ingredients of Phase B. Heat each phase to 73 C-78° C. while mixing each phase using a suitable mixer (e.g. Anchor blade, propeller blade, IKA T25) until each reaches temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21° C. and 33° C.

Example 5

A series of comparative experiments were conducted to demonstrate aspects of the present invention. These experiments are based upon testing of the formulas outlined under Table I.

TABLE I

| | Formula (Weight %) | | | | | | | |
|---|---|---|---|---|---|---|---|---|
| Component | 1 | 2 | 3 | 4 | 5 | 6 | 7 | 8 |
| Water Phase | | | | | | | | |
| Polysorbate 40 | 1.62 | 1.62 | 1.62 | 1.62 | 1.62 | 1.62 | 1.62 | 1.62 |
| Cetyl Alcohol | 1.55 | 1.55 | 1.55 | 1.55 | 1.55 | 1.55 | 1.55 | 1.55 |
| Glycerin Monostearate | 0.78 | 0.78 | 0.78 | 0.78 | 0.78 | 0.78 | 0.78 | 0.78 |
| Linoleic Acid | 0.10 | 0.10 | 0.10 | 0.10 | 0.10 | 0.10 | 0.10 | 0.10 |
| Stearic Acid | 0.25 | 0.25 | 0.25 | 0.25 | 0.25 | 0.25 | 0.25 | 0.25 |
| Cholesterol | 0.20 | 0.20 | 0.20 | 0.20 | 0.20 | 0.20 | 0.20 | 0.20 |
| Glycerin | 9.00 | 9.00 | 9.00 | 9.00 | 9.00 | 9.00 | 9.00 | 9.00 |
| Water | Qs | Qs | Qs | Qs | Qs | Qs | Qs | Qs |
| Sunscreens | | | | | | | | |
| UV Pearls ™ | — | — | — | 5.50 | — | — | — | — |
| SunCaps 664 ™ | — | — | — | — | 9.50 | — | — | — |
| Sylvaclear PA 1200V ™ (1:1 with OMC) | — | — | — | — | — | 4.00 | — | — |
| Sylvaclear PA 1200V ™ (polymer only) | — | — | — | — | — | — | 4.00 | 4.00 |
| Parsol ® MCX (Octylmethoxycinnamate) | 6.00 | 2.00 | — | — | — | — | — | 2.00 |
| Oil Phase | | | | | | | | |
| DC 200 (Dimethicone) | 1.00 | 5.00 | 7.00 | 7.00 | 7.00 | 7.00 | 7.00 | 25.00 |
| DC5225C (Dimethicone Copolyol/Cyclomethicone) | 0.50 | 0.50 | 0.50 | 0.50 | 0.50 | 0.50 | 0.50 | 0.50 |
| DC9045 (Silicone Elastomer) | 20.00 | 20.00 | 20.00 | 20.00 | 20.00 | 20.00 | 20.00 | — |
| Polymers | | | | | | | | |
| Aristoflex AVC (Taurate Copolymer) | 0.80 | 0.80 | 0.80 | 0.80 | 0.80 | 0.80 | 0.40 | 0.40 |
| Particulates | | | | | | | | |
| Z-cote HP-1 (Zinc Oxide) | | | | | | | | |
| Titanium Dioxide | 2.00 | 2.00 | 2.00 | 2.00 | 2.00 | 2.00 | 2.00 | 2.00 |
| Ganzpearl GMP-0820 (Polymethylmethacrylate) | 0.50 | 0.50 | 0.50 | 0.50 | 0.50 | 0.50 | 0.50 | 0.50 |
| Luminosity Powder | | | | | | | | |
| Satin Mica | 0.50 | 0.50 | 0.50 | 0.50 | 0.50 | 0.50 | 0.50 | 0.50 |
| Timiron MP 111 (Titanium Dioxide Coated Mica) | 1.00 | 1.00 | 1.00 | 1.00 | 1.00 | 1.00 | 1.00 | 1.00 |

Optical Measurements

Opacity is the measure of intensity attenuation of a transmitted light beam shone perpendicular to a medium or film. The higher the direct beam attenuation, the greater will be the opacity. The source of the light beam attenuation is two fold: A) Some of the original light is reflected back from the film/medium. This gives the film/medium a true white/opaque appearance with great hiding power. Using pigment-grade $TiO_2$ in a formulation will give the effect. B) Some of the light is deflected from the straight beam path but still transmitted through the film/medium. In effect, the film/medium goes from being transparent to translucent, creating a "blurred" image. Another term for this is soft focus.

Procedure: Apply (or draw down) a 3 mil (76.2 μm) film of a formulation using a draw down bar on to a plastic overhead transparency sheet. Let the film dry for 2 hours at room temperature. Take the coated overhead transparency and place it in an Instrument Systems goniospectrophotometer. Set the light source and detector arrayed in a straight line perpendicular to the coated transparency. The light source (set at 209 million Watt-nm/cm$^2$, which serves as a reference for all Transmission Intensity Values reported herein) is turned on and the measurement of the transmitted light intensity is made. Further measurements are made by moving the detector 10, 30, 40, 50 degrees away from the direct transmission normal. These values indicate the extent of soft focus light scattering. The Reflectance or "radiance" of a product is determined in the same way as opacity/soft focus light scattering, except for the positions of the light source and detector. The detector is 30 degrees on one side of the normal/perpendicular, while the light source is 20 degrees on the other side. To determine the extent of the intensity attenuation, compare the intensity value to that of an uncoated overhead transparency. The difference between these two values is the extent of the attenuation or opacity.

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formula is applied to a plate using an 1 mil draw-down applicator. This leaves a film of 2 mg/cm$^2$. The film is left to dry for 30 minutes. Subsequently an SPF reading is taken on the dried film using three measurements on different parts of the coated quartz plate and recording an average value.

Soft focus results with the formulations are reported in Table II.

TABLE II

Transmission Intensity Values*

| | Formula | | | | | | | | |
|---|---|---|---|---|---|---|---|---|---|
| | 1 | 2 | 3 | 4 | 5 | 6 | 7 | 8 | 9 |
| Variable Component | 6% External OMC** | 2% External OMC | 0% OMC | UV Pearls | SunCaps 664 | Sylvaclear OMC Composite | Sylvaclear With No OMC | Sylvaclear and 2% External OMC | Formula 6 without Elastomer |
| Transmission Angle in Degrees | | | | | | | | | |
| 0 | 6.6 M | 6.3 M | 5.0 M | 4.2 M | 4.1 M | 4.4 M | 4.4 M | 6.4 M | 11 M |
| 10 | 1.0 M | 1.1 M | 1.7 M | 1.8 M | 1.8 M | 1.9 M | 1.9 M | 1.1 M | 1.0 M |
| 30 | 121K | 127K | 137K | 140K | 139K | 140K | 140K | 128K | 88K |
| 40 | 61K | 65K | 73K | 80K | 79K | 79K | 79K | 70K | 47K |
| 50 | 40K | 43K | 49K | 58K | 60K | 59K | 59K | 47K | 32K |
| Reflection Angle in Degrees | | | | | | | | | |
| 30 | 143K | 153K | 160K | 165K | 164K | 167K | 167K | 157K | 176K |
| SPF Value | 15 | 8 | 4 | 17 | 32 | 16 | 4 | 8 | 15 |

*Values are the Intensity of light scatter (units are W-nm/cm2)
**OMC is Octylmethoxycinnamate (sunscreen agent)

All the composites (UV Pearls, SunCaps, Sylvaclear/Sunscreen) were formulated to deliver 2% Octylmethoxycinnamate (OMC) to the overall cosmetic composition.

As the OMC sunscreen agent concentration (non-composite) is increased, the soft focus transmission profile tends lower. For instance, Formulas 1, 2 and 3 illustrate a progression of increasing Transmission Intensity Values throughout the range of reported angles.

Composite particles (the hydrophilic particles of binder/sunscreen agent) not only maintain the soft focus benefits of the 0% OMC (Formula 3) but also exhibit improved (increased) high angle soft focus profile. This is seen in the favorable comparison of higher Transmission Intensity Values for Formulas 4, 5 and 6 against Formula 3. Moreover, Formulas 4, 5 and 6 all have an SPF higher than 15 (achieved with only a 2% OMC loading by weight of the cosmetic composition). Also of note is that the composites improved (lowered) opacity and increased reflectance. Formula 9 is identical to Formula 6 except that the former contains no crosslinked silicone elastomer. Absent the elastomer, the formula at several Transmission angles exhibits lower performance values.

What is claimed is:
1. A cosmetic composition comprising:
   (i) from about 0.1 to about 20% by weight of hydrophilic composite particles comprising octylmethoxycinnamate as a organic sunscreen agent and a binder in a ratio of about 5:1 to about 1:10 wherein the binder is a polyalkylenoxypolyamide;

(ii) from about 0.1 to about 30% by weight of particles of a crosslinked silicone elastomer; and (iii) a cosmetically acceptable carrier.

2. The composition according to claim 1 wherein the sunscreen agent and binder are intimately mixed together to form each of the composite particles.

3. The composition according to claim 1 wherein the hydrophilic composite particles have an average particle size ranging from about 10 to about 2,000 nm.

4. The composition according to claim 1 wherein the hydrophilic composite particles have an average particle size ranging from about 100 to about 1,500 nm.

5. The composition according to claim 1 wherein the sunscreen agent further comprises Benzophenone-3.

6. The composition according to claim 1 wherein the crosslinked silicone elastomer has a particle size ranging from about 25,000 to about 55,000 nm.

7. A cosmetic composition comprising:
(i) from about 2 to about 15% by weight of hydrophilic composite particles having an average particle size ranging from about 10 to about 2,000 nm and comprising organic sunscreen agent and a binder in a ratio of about 5:1 to about 1:10, the binder being a polyalkyleneoxypolyamide; and the sunscreen agent is octylmethoxycinnamate (ii) from about 0.1 to about 30% by weight of particles of a crosslinked silicone elastomer; and (iii) a cosmetically acceptable carrier.

* * * * *